(12) United States Patent
Hewick et al.

(10) Patent No.: US 7,378,392 B1
(45) Date of Patent: May 27, 2008

(54) BONE AND CARTILAGE INDUCTIVE PROTEINS

(75) Inventors: Rodney M. Hewick, Lexington, MA (US); Jack H. Wang, Lexington, MA (US); John M. Wozney, Hudson, MA (US); Anthony J. Celeste, Hudson, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 08/319,831

(22) Filed: Oct. 6, 1994

Related U.S. Application Data

(60) Division of application No. 07/800,364, filed on Nov. 26, 1991, now Pat. No. 5,688,678, and a continuation-in-part of application No. 07/641,204, filed on Jan. 15, 1991, now abandoned, and a continuation-in-part of application No. 07/525,357, filed on May 16, 1990, now abandoned.

(30) Foreign Application Priority Data

May 15, 1991    (WO) ..................... PCT/US91/03388

(51) Int. Cl.
*A61K 38/18* (2006.01)
*C07K 14/435* (2006.01)
*C07K 14/51* (2006.01)

(52) U.S. Cl. .................... 514/12; 514/2; 514/7; 514/8; 530/350; 530/351; 530/352; 530/395; 530/397; 530/399

(58) Field of Classification Search ................ 530/350, 530/395, 399, 300; 435/69.1, 69.4; 424/422, 424/423, 425, 426; 514/12, 21, 2; 536/23.51, 536/23.5
See application file for complete search history.

(56) References Cited

U.S. PATENT DOCUMENTS

| | | | |
|---|---|---|---|
| 4,294,753 A | 10/1981 | Urist | 530/395 |
| 4,434,094 A | 2/1984 | Seyedin et al. | 530/416 |
| 4,455,256 A | 6/1984 | Urist | 530/350 |
| 4,563,350 A | 1/1986 | Nathan | 424/95 |
| 4,608,199 A | 8/1986 | Caplan et al. | 530/414 |
| 4,619,989 A | 10/1986 | Urist | 530/417 |
| 4,627,982 A | 12/1986 | Seyedin et al. | 424/95 |
| 4,681,763 A | 7/1987 | Nathanson | 424/95 |
| 4,737,578 A | 4/1988 | Evans | 530/350 |
| 4,761,471 A | 8/1988 | Urist | 530/350 |
| 4,774,228 A | 9/1988 | Seyedin | 514/21 |
| 4,774,322 A | 9/1988 | Seyedin | 530/353 |
| 4,789,732 A | 12/1988 | Urist | 530/350 |
| 4,795,804 A | 1/1989 | Urist | 530/350 |
| 4,798,885 A | 1/1989 | Mason | 530/350 |
| 4,804,744 A | 2/1989 | Sen | 530/350 |
| 4,810,691 A | 3/1989 | Seyedin | 514/2 |
| 4,843,063 A | 6/1989 | Seyedin | 514/2 |
| 4,886,747 A | 12/1989 | Derynck | 435/69.4 |
| 4,968,590 A | 11/1990 | Kuberasampath et al. | 530/326 |
| 5,011,691 A | 4/1991 | Oppermann | 424/423 |
| 5,106,626 A | 4/1992 | Parsons et al. | |
| 5,108,753 A | 4/1992 | Kuberasampath | 424/422 |
| 5,266,683 A * | 11/1993 | Oppermann et al. | 530/326 |
| 5,354,557 A * | 10/1994 | Oppermann et al. | 424/423 |

FOREIGN PATENT DOCUMENTS

| | | |
|---|---|---|
| CA | 2 017466 | 5/1990 |
| EP | 33 6760 | 6/1989 |
| EP | 4 165 78 A2 | 5/1990 |
| EP | 4 094 72 A1 | 11/1990 |
| WO | WO 89/09787 | 10/1989 |
| WO | WO 89/09788 | 10/1989 |
| WO | WO 90/03733 | 4/1990 |
| WO | WO 91/02744 | 3/1991 |
| WO | WO 91/05802 | 5/1991 |
| WO | WO 92/07004 | 4/1992 |
| WO | WO 92/07073 | 4/1992 |
| WO | WO 93/04692 | 3/1993 |
| WO | WO 93/05751 | 4/1993 |
| WO | WO 91/18047 | 11/1999 |

OTHER PUBLICATIONS

Zoller et al. 1983. Methods in Enzymology, 100:468-500.*
Urist et al., *Science*, 220: 680-686 (1983).
Luyten et al., *The Journal of Biological Chemistry*, 264(23) 13377-13380 (Aug. 15, 1989).
Sampath, et al., *Proc. Natl. Acad. Sci*, 84: 7109-7113 (1987).
Ozkaynak et al., *The EMBO Journal*, v.9 No. 7: 2085-2093 (1990).
Hammonds et al., *Molecular Endocrinology*, 5:149-155 (1991).

* cited by examiner

*Primary Examiner*—Elizabeth C. Kemmerer
(74) *Attorney, Agent, or Firm*—Finnegan, Henderson, Farabow, Garrett & Dunner, LLP

(57) ABSTRACT

Purified cartilage and/or bone inductive proteins and processes for producing them are disclosed. The proteins may be used in the treatment of bone and/or cartilage defects and in wound healing and related tissue repair.

6 Claims, 3 Drawing Sheets

Figure 2

```
          (1)
GAATTCC GAG CCC CAT TGG AAG GAG TTC CGC TTT GAC CTG ACC CAG ATC CCG GCT
        Glu Pro His Trp Lys Glu Phe Arg Phe Asp Leu Thr Gln Ile Pro Ala
        (1)                                 (10)

GGG GAG GCG GTC ACA GCT GCG GAG TTC CGG ATT TAC AAG GTG CCC AGC ATC CAC
Gly Glu Ala Val Thr Ala Ala Glu Phe Arg Ile Tyr Lys Val Pro Ser Ile His
            (20)                                    (30)

CTG CTC AAC AGG ACC CTC CAC GTC AGC ATG TTC CAG GTG GTC CAG GAG CAG TCC
Leu Leu Asn Arg Thr Leu His Val Ser Met Phe Gln Val Val Gln Glu Gln Ser
                (40)                                        (50)

AAC AGG GAG TCT GAC TTG TTC TTT TTG GAT CTT CAG ACG CTC CGA GCT GGA GAC
Asn Arg Glu Ser Asp Leu Phe Phe Leu Asp Leu Gln Thr Leu Arg Ala Gly Asp
                        (60)                                        (70)

GAG GGC TGG CTG GTG CTG GAT GTC ACA GCA GCC AGT GAC TGC TGG TTG CTG AAG
Glu Gly Typ Leu Val Leu Asp Val Thr Ala Ala Ser Asp Cyc Trp Leu Leu Lys
                                    (80)

CGT CAC AAG GAC CTG GGA CTC CGC CTC TAT GTG GAG ACT GAG GAT GGG CAC AGC
Arg His Lys Asp Leu Gly Lue Arg Leu Tyr Val Glu Thr Glu Asp Gly His Ser
    (90)                                    (100)

GTG GAT CCT GGC CTG GCC GGC CTG CTG GGT CAA CGG GCC CCA CGC TCC CAA CAG
Val Asp Pro Gly Leu Ala Gly Leu Leu Gly Gln Arg Ala Pro Arg Ser Gln Gln
            (110)                                       (120)

CCT TTC GTG GTC ACT TTC TTC AGG GCC AGT CCG AGT CCC ATC CGC ACC CCT CGG
Pro Phe Val Val Thr Phe Phe Arg Ala Ser Pro Ser Pro Ile Arg Thr Pro Arg
                (130)                                       (140)
(450)
GCA GTG AGG CCA CTG AGG AGG AGG CAG CCG AAG AAA AGC AAC GAG CTG CCG CAG
Ala Val Arg Pro Leu Arg Arg Arg Gln Pro Lys Lys Ser Asn Glu Leu Pro Gln
(143)                   (150)                                       (160)

GCC AAC CGA CTC CCA GGG ATC TTT GAT GAC GTC CAC GGC TCC CAC GGC CGG CAG
Ala Asn Arg Leu Pro Gly Ile Phe Asp Asp Val His Gly Ser His Gly Arg Gln
                                        170)

GTC TGC CGT CGG CAC GAG CTC TAC GTC AGC TTC CAG GAC CTT GGC TGG CTG GAC
Val Cys Arg Arg His Glu Leu Tyr Val Ser Phe Gln Asp Leu Gly Trp Leu Asp
    (180)                                   (190)

TGG GTC ATC GCC CCC CAA GGC TAC TCA GCC TAT TAC TGT GAG GGG GAG TGC TCC
Trp Val Ile Ala Pro Gln Gly Tyr Ser Ala Tyr Tyr Cys Glu Gly Glu Cys Ser
            (200)                                       (210)
```

Figure 2 (Con't)

```
TTC CCG CTG GAC TCC TGC ATG AAC GCC ACC AAC CAC GCC ATC CTG CAG TCC CTG
Phe Pro Leu Asp Ser Cys Met Asn Ala Thr Asn His Ala Ile Leu Gln Ser Leu
                (220)                                        (230)

GTG CAC CTG ATG AAG CCA AAC GCA GTC CCC AAG GCG TGC TGT GCA CCC ACC AAG
Val His Leu Met Lys Pro Asn Ala Val Pro Lys Ala Cys Cys Ala Pro Thr Lys
                    (240)                                        (250)

CTG AGC GCC ACC TCT GTG CTC TAC TAT GAC AGC AGC AAC AAC GTC ATC CTG CGC
Leu Ser Ala Thr Ser Val Leu Tyr Tyr Asp Ser Ser Asn Asn Val Ile Leu Arg
                            (260)
                                                    (843)
AAG CAC CGC AAC ATG GTG GTC AAG GCC TGC GGC TGC CAC TGAGTCAGCCCGCCCAGC
Lys His Arg Asn Met Val Val Lys Ala Cys Gly Cys His
    (270)                                    (280)

CCTACTGCAGCCACCCTTCTCATCTGGATCGGGCCCTGCAGAGGCAGAAAACCCTTAAATGCTGTCACAG

CTCAAGCAGGAGTGTCAGGGGCCCTCACTCTCGGTGCCTACTTCCTGTCAGGCTTCTGGGAATTC
```

BONE AND CARTILAGE INDUCTIVE PROTEINS

This is a division, of application Ser. No. 07/800,364 filed Nov. 26, 1991 now U.S. Pat. No. 5,688,678 which is a continuation-in-part of U.S. Ser. No. 07/525,357 filed May 16, 1990 now abandoned and U.S. Ser. No. 07/641,204 filed Jan. 15, 1991. This application also claims priority of PCT/US91/03388.

The present invention relates to a family of purified proteins which may exhibit the ability to induce cartilage and/or bone formation and processes for obtaining them. These proteins may be used to induce bone and/or cartilage formation and in wound healing and tissue repair.

The invention provides a novel family of proteins termed BMP-8 proteins. Bovine and perhaps other species BMP-8 proteins are characterized by comprising at least one of the same or substantially the same amino acid sequences comprising (1). Arg-His-Glu-Leu-Tyr-Val-Ser-Phe-Gln-Asp-Leu-Gly-Trp-Leu-Asp-Trp-Val-Ile-Ala-Pro-Gln-Gly-Tyr (SEQ ID NO: 1)

(2). Leu-Ser-Ala-Thr-Ser-Val-Leu-Tyr-Tyr-Asp-Ser-Ser-Asn-Asn-Val-Ile-Leu-Arg (SEQ ID NO: 2)

(3). Ala-Cys-Cys-Ala-Pro-Thr-Lys (SEQ ID NO: 3)

(4). Thr-Asn-Glu-Leu-Pro-Pro-Pro-Asn-Lys-Leu-Pro-Gly-Ile-Phe-Asp-Asp-Val-His-Gly-Ser-His-Gly-Arg (SEQ ID NO: 4)

Human BMP-8 proteins are characterized by the amino acid sequence disclosed in SEQ ID NO: 14. Human BMP-8 proteins may be further characterized as disulfide-linked dimers of mature BMP-8 subunits. Recombinantly-expressed BMP-8 subunits may include protein species having heterogeneous amino termini. A BMP-8 sequence or subunit sequence comprises amino acid #4 (Ala)-#142 (His) of SEQ ID NO: 14 of FIG. 2. Other amino termini of BMP-8 may be selected from the sequence of SEQ ID NO: 14. Modified versions, including proteins further truncated at the amino or carboxy termini, of BMP-8 may also be constructed by resort to conventional mutagenic techniques.

The BMP-8 proteins of the invention may be further characterized by an apparent molecular weight of 28,000-38,000 daltons as determined by sodium dodecyl sulfate polyacrylamide gel electrophoresis (SDS-PAGE). Under reducing conditions in SDS-PAGE the protein reveals a region of approximately 14,000-20,000 daltons.

The BMP-8 proteins may be further characterized by a DNA sequence encoding BMP-8 comprising at least one of the following DNA sequences (1) GTC CAC CTG CTG AAG CCG CAC GCG GTC CCC AAG GCG TGC TGC GCG CCC ACC AAG CTG AGC GCC ACT TCC GTC CTC TAC TAC GAC AGC AGC AAC AAC GTC ATC CTG CGC AAG CAC CGC AAC ATG GTC GTC CGC GCC TGC GGC TGC CAC (SEQ ID NO: 7)

(2) GAC TGG GTC ATC GCC CCC CAA GGC TAC TCA GCC TAT TAC TGT GAA GGG GAG TGC TCC TTC CCG CTG GAC TCC TGC ATG AAC GCC ACC AAC CAC GCC ATC CTG CAG TCC CTG (SEQ ID NO: 9)

(3) GAC GTC CAC GGC TCC CAC GGC CGG CAG GTC TGC CGT CGG CAC GAG CTG AGC TTC CAG GAC CTG GGC TGG CTG (SEQ ID NO: 11)

Human BMP-8 proteins may be characterized by a DNA sequence comprising nucleotide #8 through #850 as set forth in SEQ ID NO: 13

It is contemplated that the proteins of the invention are capable of stimulating, promoting, or otherwise inducing cartilage and/or bone formation.

The invention further includes methods for obtaining the DNA sequences encoding the BMP-8 proteins of the invention. This method entails utilizing the above amino acid sequences or portions thereof to design probes as well as the disclosed DNA sequences to screen libraries.

The proteins of the invention may be produced by culturing a cell transformed with a DNA sequence encoding the BMP-8 protein and recovering and purifying from the culture medium a protein characterized by comprising at least one of the same or substantially the same amino acid sequences comprising (1). Arg-His-Glu-Leu-Tyr-Val-Ser-Phe-Gln-Asp-Leu-Gly-Trp-Leu-Asp-Trp-Val-Ile-Ala-Pro-Gln-Gly-Tyr (SEQ ID NO: 1)

(2). Leu-Ser-Ala-Thr-Ser-Val-Leu-Tyr-Tyr-Asp-Ser-Ser-Asn-Asn-Val-Ile-Leu-Arg (SEQ ID NO: 2)

(3). Ala-Cys-Cys-Ala-Pro-Thr-Lys (SEQ ID NO: 3)

(4). Thr-Asn-Glu-Leu-Pro-Pro-Pro-Asn-Lys-Leu-Pro-Gly-Ile-Phe-Asp-Asp-Val-His-Gly-Ser-His-Gly-Arg (SEQ ID NO: 4)

(5) Ala-Val-Arg-Pro-Leu-Arg-Arg-Arg-Gln-Pro-Lys-Lys-Ser-Asn-Glu-Leu-Pro-Gln-Ala-Asn-Arg-Leu-Pro-Gly-Ile-Phe-Asp-Asp-Val-His-Gly-Ser-His-Gly-Arg-Gln-Val-Cys-Arg-Arg-His-Glu-Leu-Tyr-Val-Ser-Phe-Gln-Asp-Leu-Gly-Trp-Leu-Asp-Trp-Val-Ile-Ala-Pro-Gln-Gly-Tyr-Ser-Ala-Tyr-Tyr-Cys-Glu-Gly-Glu-Cys-Ser-Phe-Pro-Leu-Asp-Ser-Cys-Met-Asn-Ala-Thr-Asn-His-Ala-Ile-Leu-Gln-Ser-Leu-Val-His-Leu-Met-Lys-Pro-Asn-Ala-Val-Pro-Lys-Ala-Cys-Cys-Ala-Pro-Thr-Lys-Leu-Ser-Ala-Thr-Ser-Val-Leu-Tyr-Tyr-Asp-Ser-Ser-Asn-Asn-Val-Ile-Leu-Arg-Lys-His-Arg-Asn-Met-Val-Val-Lys-Ala-Cys-Gly-Cys-His

The above sequence (5) representing amino acid #4 to #142 of SEQ ID NO: 14

The expressed protein is isolated, recovered and purified from the culture medium. The purified expressed protein is substantially free from other proteinaceous materials with which it is co-produced, as well as from other contaminants. The recovered purified protein is contemplated to exhibit cartilage and/or bone formation activity.

Human BMP-8 may be produced by culturing a cell transformed with a DNA sequence comprising the nucleotide coding sequence from nucleotide #8 to #850 of SEQ ID NO: 13 and recovering and purifying from the culture medium a protein comprising amino acid #4 to #142 of SEQ ID NO: 14, or similar amino acid sequences with heterogenous N-termini, substantially free from other proteinaceous materials or other contaminating materials with which it is co-produced. This BMP-8 may also be produced in E. coli by inserting into a vector the sequence encoding amino acid #143 to #281 of with a Met inserted before amino acid #143.

The proteins of the invention may be further characterized by the ability to demonstrate cartilage and/or bone formation activity in the rat bone formation assay described below. It is further contemplated that the proteins of the invention demonstrate activity in this rat bone formation assay at a concentration of 0.5µ-500 µg/gram of bone formed. It is further contemplated that these proteins demonstrate activity in this assay at a concentration of 1 µg-50 µg/gram bone. More particularly, it is contemplated these proteins may be characterized by the ability of 1 µg of the protein to score at least +2 in the rat bone formation assay.

Another aspect of the invention provides pharmaceutical compositions containing a therapeutically effective amount of a protein of the invention in a pharmaceutically acceptable vehicle or carrier. The compositions of the invention may be used to induce bone and/or cartilage formation. These compositions may also be used for wound healing and tissue repair. Further compositions of the invention may include in addition to a protein of the present invention at least one other therapeutically useful agent such as the proteins designated BMP-1, BMP-2 (also previously referred to as BMP-2A or BMP-2 Class I), BMP-3, BMP-4 (also previously referred to as BMP-2B or BMP-2 Class II) disclosed in PCT publications WO 88/00205 and WO 89/10409; and BMP-5, BMP-6, and BMP-7 disclosed in PCT publication WO 90/11366.

Other therapeutically useful agents include growth factors such as epidermal growth factor (EGF), fibroblast growth factor (FGF), and transforming growth factors (TGF-α and TGF-β). The compositions of the invention may also include an appropriate matrix, for instance, for supporting the composition and/or providing a surface for bone and/or cartilage growth. The matrix may provide slow release of the BMP protein and or the appropriate environment for presentation of the BMP protein.

The compositions may be employed in methods for treating a number of bone and/or cartilage defects, and periodontal disease. They may also be employed in methods for treating various types of wounds and in tissue repair. These methods, according to the invention, entail administering to a patient needing such bone and/or cartilage formation, wound healing or tissue repair, a therapeutically effective amount of a protein of the invention. These methods may also entail the administration of a protein (or portion thereof) of the invention in conjunction with at least one of the "BMP" proteins (or portion thereof) disclosed in the co-owned applications described above. In addition, these methods may also include the administration of a protein of the invention with other growth factors including EGF, FGF, TGF-a, and TGF-b.

Still a further aspect of the invention are DNA sequences coding for expression of a BMP-8 protein of the invention. Such sequences include a sequence of nucleotides encoding at least one of the same or substantially the same peptide sequences reported above or fragments thereof. DNA sequences of the invention include the following DNA sequences:

(1) GTG CAG CTG CTG AAG CCG CAC GCG GTC CCC AAG GCG TGC TGC GCG CCC ACC AAG CTG AGC GCC ACT TCC GTG CTC TAC TAC GAC AGC AGC AAC AAC GTC ATC CTG CGC AAG CAC CGC AAC ATG GTG GTC CGC GCC TGC GGC TGC CAC (SEQ ID NO: 7)

(2) GAC TGG GTC ATC GCC CCC CAA GGC TAC TCA GCC TAT TAC TGT GAA GGG GAG TGC TCC TTC CCG CTG GAC TCC TGC ATG AAC GCC ACC AAC CAC GCC ATC CTG CAG TCC CTG (SEQ ID NO: 9)

(3) GAC GTC CAC GGC TCC CAC GGC CGG GAG GTG TGC CGT CGG CAC GAG CTG AGC TTC AGG GAC CTG GGC TGG CTG (SEQ ID NO: 11)

and the DNA sequence of SEQ ID NO: 13

A further aspect of the invention provides vectors containing a DNA sequence encoding BMP-8 proteins of the invention as described above in operative association with an expression control sequence therefor. Host cells transformed with such vectors for use in producing BMP-8 proteins are also provided by the present invention. The host cells containing DNA sequences encoding BMP-8 may be employed in a novel process for producing a protein of the invention. The transformed host cells are cultured in a suitable culture medium and a protein of the invention is isolated and purified from the cells, cell lysate, or conditioned medium by conventional techniques. This process may employ a number of known cells, both prokaryotic and eukaryotic, as host cells for expression of the polypeptide.

Other aspects and advantages of the present invention will be apparent upon consideration of the following detailed description and preferred embodiments thereof.

BRIEF DESCRIPTION OF THE DRAWING

FIG. 2 (SEQ ID NOS: 13 and 14) comprises nucleotide and amino acid sequence of human BMP-8.

DETAILED DESCRIPTION OF THE INVENTION

Figure 1:
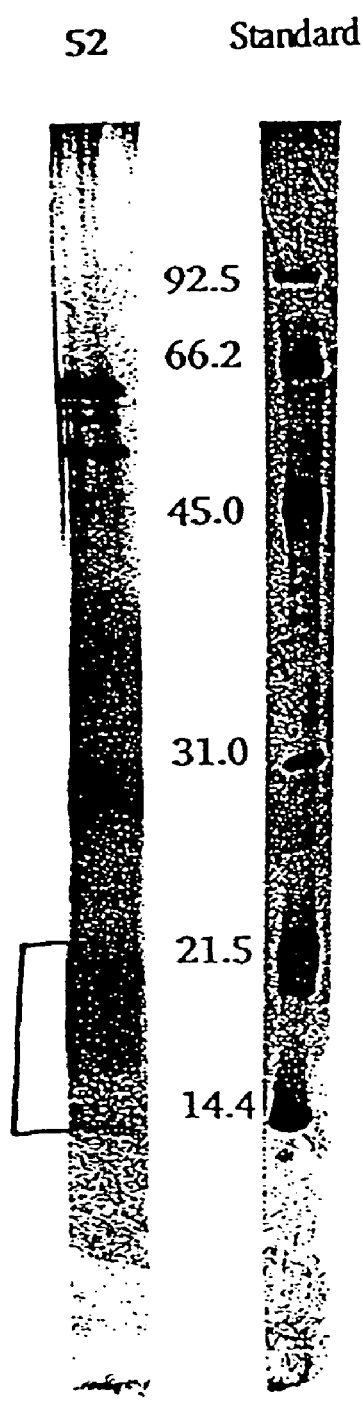
FIG. 1 illustrates an SDS-PAGE analysis of an osteoinductive fraction (28,000-38,000 daltons non-reduced) following reduction with dithiothreitol.

A purified BMP-8 cartilage/bone protein of the present invention is characterized by comprising at least one of the same or substantially the same amino acid sequences comprising (1). Arg-His-Glu-Leu-Tyr-Val-Ser-Phe-Gln-Asp-Leu-Gly-Trp-Leu-Asp-Trp-Val-Ile-Ala-Pro-Gln-Gly-Tyr (SEQ ID NO: 1)
(2). Leu-Ser-Ala-Thr-Ser-Val-Leu-Tyr-Tyr-Asp-Ser-Ser-Asn-Asn-Val-Ile-Leu-Arg (SEQ ID NO: 2)
(3). Ala-Cys-Cys-Ala-Pro-Thr-Lys (SEQ ID NO: 3)
(4). Thr-Asn-Glu-Leu-Pro-Pro-Pro-Asn-Lys-Leu-Pro-Gly-Ile-Phe-Asp-Asp-Val-His-Gly-Ser-His-Gly-Arg (SEQ ID NO: 4)
(5) amino acid #4 through #142 of SEQ ID NO: 14.

Human BMP-8 proteins may be further characterized as disulfide-linked dimers of mature BMP-8 subunits. Recombinantly-expressed BMP-8 subunits may include protein species having heterogeneous amino termini. A BMP-8 sequence or subunit sequence comprises amino acid #4 (Ala)-#142 (His) of SEQ ID NO: 14. Other amino termini of BMP-8 may be selected from the sequence of SEQ ID NO: 14. Modified versions, including proteins further truncated at the amino or carboxy termini, of BMP-8 may also be constructed by resort to conventional mutagenic techniques. Human BMP-8 proteins are characterized by the amino acid sequence disclosed in SEQ ID NO: 14.

Purified BMP-8 proteins are substantially free from proteinaceous materials with which they are co-produced as well as from other contaminants. These proteins may be further characterized by the ability to induce cartilage and/or bone formation. It is contemplated that this activity may be demonstrated by activity in the rat bone formation assay as described in Example III. It is further contemplated that these proteins demonstrate activity in the assay at a concentration of 0.5μ-500 μg/gram of bone formed. It is further contemplated that these proteins demonstrate activity in this assay at a concentration of 1 μg-50 μg/gram bone. The proteins may be further characterized by the ability of 1 μg to score at least +2 in this assay using either the original or modified scoring method.

The proteins of the invention are further characterized by an apparent molecular weight of 28,000-38,000 daltons as determined by sodium dodecyl sulfate polyacrylamide gel electrophoresis (SDS-PAGE). Under reducing conditions in SDS-PAGE the protein reveals a region of approximately 14,000-20,000 daltons.

In a further aspect, the invention provides a method for obtaining the DNA sequences encoding BMP-8 bone/cartilage proteins of the invention. The method for obtaining the DNA sequences entails utilizing the amino acid sequences described above to design probes as well as the disclosed nucleotide sequences to screen libraries using standard techniques.

The proteins provided herein also include factors encoded by the above described sequences but into which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of the proteins of the BMP-8 proteins are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein involve modifications of the glycosylation site. These modifications may involve O-linked or N-linked glycosylation sites. For instance, the absence of glycosylation or only partial glycosylation results from amino acid substitution or deletion at the asparagine-linked glycosylation recognition sites present in the sequences of the proteins of the invention. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences procedures variants which are not glycosylated at that site.

The present invention also encompasses the novel DNA sequences, free of association with DNA sequences encoding other proteinaceous materials, and coding on expression for BMP-8 the proteins of the invention. Further included are those sequences which hybridize under stringent hybridization conditions [see, T. Maniatis et al, *Molecular Cloning (A Laboratory Manual)*, Cold Spring Harbor Laboratory (1982), pages 387 to 389 ] to the DNA sequences isolated in accordance with the procedure described above and demonstrate cartilage and/or bone formation activity in the rat bone formation assay. An example of one such stringent hybridization condition is hybridization at 4× SSC at 65° C., followed by a washing in 0.1× SCC at 65° C. for an hour. Alternatively, an exemplary stringent hybridization condition is in 50% formamide, 4× SCC at 42° C.

Similarly, DNA sequences isolated as described above which encode BMP-8 proteins, but which differ in codon sequence due to the degeneracies of the genetic code or allelic variations (naturally-occurring base changes in the species population which may or may not result in an amino acid change) also encode the proteins of the invention described herein. Variations in the DNA sequences which are caused by point mutations or by induced modifications (including insertion, deletion, and substitution) to enhance the activity, half-life or production of the polypeptides encoded thereby are also encompassed in the invention.

Another aspect of the present invention provides a novel method for producing the proteins of the invention. This method involves culturing a suitable cell line, which has been transformed with a DNA sequence coding for expression of a protein of the invention, under the control of known regulatory sequences. Regulatory sequences include promoter fragments, terminator fragments and other suitable sequences which direct the expression of the BMP-8 protein in an appropriate host cell. A purified BMP-8 protein of the present invention is recovered, isolated and purified from the culture medium. The purified protein is characterized by comprising at least one of the same or substantially the same amino acid sequences comprising (1). Arg-His-Glu-Leu-Tyr-Val-Ser-Phe-Gln-Asp-Leu-Gly-Trp-Leu-Asp-Trp-Val-Ile-Ala-Pro-Gln-Gly-Tyr (SEQ ID NO: 1)

(2). Leu-Ser-Ala-Thr-Ser-Val-Leu-Tyr-Tyr-Asp-Ser-Ser-Asn-Asn-Val-Ile-Leu-Arg (SEQ ID NO: 2)

(3). Ala-Cys-Cys-Ala-Pro-Thr-Lys (SEQ ID NO: 3)

(4). Thr-Asn-Glu-Leu-Pro-Pro-Pro-Asn-Lys-Leu-Pro-Gly-Ile-Phe-Asp-Asp-Val-His-Gly-Ser-His-Gly-Arg (SEQ ID NO: 4)

(5). amino acid #4 through #142 or SEQ ID NO: 14.

Human BMP-8 proteins are characterized by the amino acid sequence disclosed in SEQ ID NO: 14. Human BMP-8 proteins may be further characterized as disulfide-linked dimers of mature BMP-8 subunits. Recombinantly-expressed BMP-8 subunits may include protein species having heterogeneous amino termini. A BMP-8 sequence or subunit sequence comprises amino acid #4 (Ala)-#142 (His) of SEQ ID NO: 14. Other amino termini of BMP-8 may be selected from the sequence of SEQ ID NO: 14. Modified versions, including proteins further truncated at the amino or carboxy termini, of BMP-8 may also be constructed by resort to conventional mutagenic techniques.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620-625 (1981), or alternatively, Kaufman et al, *Mol. Cell. Biol.*, 5(7):1750-1759 (1985) or Howley et al, U.S. Pat. No. 4,419,446. Another suitable mammalian cell line, which is described in the accompanying examples, is the monkey COS-1 cell line. The mammalian cell CV-1 may also be suitable. Further exemplary mammalian host cells include particularly primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived form Swiss, Balb-c or NIH mice, BHK or HaK hamster cell lines.

Bacterial cells may also be suitable hosts. For example, the various strains of *E. coli* (e.g., HB101, MC1061) are well-know as host cells in the field of biotechnology. Various strains of *B. subtilia, Pseudomonas,* other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering,* 8:277-298 (Plenum Press 1986) and references cited therein.

Another aspect of the present invention provides vectors for use in the method of expression of the proteins of the invention. Preferably the vectors contain the full novel BMP-8 DNA sequences described above which code for the novel cartilage/bone proteins of the invention. Additionally, the vectors also contain appropriate expression control sequences permitting expression of the protein sequences. Alternatively, vectors incorporating truncated or otherwise modified sequences as described above are also embodiments of the present invention and useful in the production of the proteins of the invention. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art and may be selected depending upon the selected host cells. Such selection is routine and does not form part of the present invention. The components of the vectors, e.g. replicons, selection genes, enhancers, promoters, and the like, may be obtained from natural sources or synthesized by known procedures. See, Kaufman et al, *J. Mol. Biol.,* 159:511-521 (1982); and Kaufman, *Proc. Natl. Acad. Sci., USA,* 82:689-693 (1985). Host cells transformed with such vectors and progeny thereof for use in producing cartilage/bone proteins are also provided by the invention.

A protein of the present invention, which induces cartilage and/or bone formation in circumstances where bone and/or cartilage is not normally formed, has application in the healing of bone fractures and cartilage defects in humans and other animals. Such application includes use in the treatment of osteoporosis. A preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO 84/01106 for discussion of wound healing and related tissue repair).

It is contemplated that proteins of the invention may increase neuronal cell survival and therefore may be useful in transplantation and conditions exhibiting a decrease in neuronal survival.

A further aspect of the invention includes therapeutic methods and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the proteins of the invention in admixture with a pharmaceutically acceptable vehicle, carrier or matrix. It is expected that the proteins of the invention may act in concert with or perhaps synergistically with one another or with other related proteins and growth factors. Therapeutic methods and compositions of the invention therefore comprise one or more of the proteins of the present invention. Further therapeutic methods and compositions of the invention therefore comprise a therapeutic amount of at least one protein of the invention with a therapeutic amount of at least one of the other "BMP" proteins disclosed in co-owned and co-pending U.S. applications described above. Such methods and compositions of the invention may comprise proteins of the invention or portions thereof in combination with the above-mentioned "BMP" proteins or portions thereof. Such combination may comprise individual molecules from each of the proteins or heteromolecules formed by portions of the respective proteins. A method and composition of the invention may therefore comprise a protein of the invention or a portion thereof linked with a portion of a different "BMP" as described above protein to form a heteromolecule. For example, a BMP-8 subunit may be linked to a subunit of BMP-2, BMP-3, BMP-4, BMP-5, BMP-6, BMP-7 or other BMP proteins. Such linkage may comprise disulfide bonds.

Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-$\alpha$ and TGF-$\beta$), and insulin-like growth factor (IGF). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone growth factor proteins. Domestic animals and thoroughbred horses in addition to humans are desired patients for such treatment with the proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition would include a matrix capable of delivering the cartilage/bone proteins of the invention to the site of bone and/or cartilage damage, providing a structure for the developing bone and cartilage and optimally capable of being reabsorbed into the body. Such matrices may be formed of materials presently in use for other implanted medical applications.

The choice of matrix material is based on biocompatibility, biodegradability, mechanical properties, cosmetic appearance and interface properties. The particular application of the compositions of the invention will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-$\alpha$, TGF-$\beta$, and IGF-I to the final composition, may also effect the dosage.

Progress can be monitored by periodic assessment of cartilage and/or bone growth and/or repair. The progress can be monitored, for example, using x-rays, histomorphometric determinations and tetracycline labeling.

The following examples illustrate practice of the present invention in recovering and characterizing bovine cartilage and/or bone proteins of the invention and employing these proteins to recover the corresponding human protein or proteins and in expressing the proteins via recombinant techniques.

Example I

Isolation of Bovine Cartilage/Bone Inductive Protein

Ground bovine bone powder (20-120 mesh, Colla-Tec) is prepared according to the procedures of M. R. Urist et al., *Proc. Natl Acad. Sci USA,* 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 4 hours in 26 liters of 0.5M EDTA. The residue is washed two times with distilled water before its resuspension in 10 liters of 4M guanidine hydrochloride [GuCl], 1 mM N-ethylmaleimide, 1 mM iodoacetic acid, 1 mM phenylmethylsulfonyl fluoride as described in *Clin. Orthop. Rel. Res.,* 171:213 (1982). After 16 to 20 hours the supernatant is removed and replaced with another 6 liters of GuCl buffer. The residue is extracted for another 8 hours. The final extraction with 6 liters of GuCl is carried out for 16 hours.

The crude GuCl extracts are combined, filtered through a Pellicon apparatus with a 0.45 mM Durapore tangential flow filter packet, concentrated approximately 50 times on a Amicon RA2000 apparatus with a 10,000 molecular weight cut-off membrane, and then dialyzed in 20 mM Tris, 0.05M NaCl, 6M urea (pH7.1), the starting buffer for the first column. After extensive dialysis the protein is loaded on a 2 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath—Reddi assay (described in Example III below) desorbed from the column by 50 mM NaAc, 0.25 mM NaCl, 6M urea (pH 4.6). The protein from this step elution is concentrated 20- to 40-fold, then dialyzed extensively against 80 mM $KPO_4$, 6M urea (pH6.0). The sample is applied to an hydroxylapatite column (IBF) equilibrated in 80 mM $KPO_4$, 6M urea (pH6.0) and all unbound protein is removed by washing the column with the same buffer. Protein having bone and/or cartilage formation activity is eluted with 100 mM $KPO_4$ (pH7.4) and 6M urea.

The protein is diluted 5 fold with a 0.1875 M NaCl, 6 M urea solution to a final concentration of 20 mM $KPO_4$, 150 mM NaCl, 6 M urea. This material is applied to a heparin—Sepharose column equilibrated in 20 mM $KPO_4$, 150 mM NaCl, 6M urea (pH7.4). After extensive washing of the column with starting buffer, a protein with bone and/or cartilage inductive activity is eluted by 20 mM $KPO_4$, 700 mM NaCl, 6M urea (pH7.4). This fraction is concentrated 10-20 fold, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). All fractions with absorbance at 280 mM are pooled. This Mono S step is now believed to be dispensable and will be eliminated in the future. The material is applied to a 4.7×30 cm Waters PrepPak 500 C4 cartridge in 0.1% TFA and the column developed with a gradient to 95% acetonitrile, 0.1% TFA in 100 minutes at 45 ml per minute. Fractions were assayed for cartilage and/or bone formation activity.

Aliquots of the appropriate fractions are iodinated by one of the following methods: P. J. McConahey et al, *Int. Arch. Allergy,* 29:185-189 (1966); A. E. Bolton et al, *Biochem J.,* 133:529 (1973); and D. F. Bowen-Pope, *J. Biol. Chem.,* 237:5161 (1982). The iodinated proteins present in these fractions are analyzed by SDS gel electrophoresis.

Example II

Characterization of Bovine Cartilage/Bone Inductive Factor

A. Molecular Weight

Approximately 2.5 mg protein from Example I from active BMP containing fractions in 0.1% TFA and approximately 45% acetonitrile, is dried with a Savant Speed Vac concentrator and solubilized with Laemmli sample buffer, loaded onto a 12.5% polyacrylamide gel and subjected to SDS-PAGE [Laemmli, U. K. *Nature,* 227:680-685 (1970)] without reducing the sample with dithiothreitol. The molecular weight is determined relative to iodinated Bio-Rad molecular weight standards. Following autoradiography of the unfixed gel the approximate 28,000-38,000 dalton band is excised and the protein electrophoretically eluted from the gel (Hunkapillar et al *Meth. Enzymol.* 91:227-236 (1983)]. Based on similar purified bone fractions as described in the co-pending "BMP" applications described above wherein bone and/or cartilage activity is found in the approximately 28,000-38,000 region, it is inferred that this band comprises bone and/or cartilage inductive fractions.

B. Subunit Characterization

The subunit composition of the isolated bovine bone protein is also determined. The eluted protein described above is fully reduced and alkylated in 2% SDS using iodoacetate and standard procedures. The fully reduced and alkylated sample is then further submitted to SDS-PAGE on a 12.5% gel and the resulting approximate 14,000-20,000 dalton region having a doublet/triplet appearance located by autoradiography of the unfixed gel. A silver stain [Merril et al, *Science,* 211:1437 (1981)] version of the sample is shown in FIG. 1 along with molecular weight markers. The 14,000-20,000 dalton region is indicated by the bracket. Thus the approximate 28,000-30,000 dalton protein yields a broad region of 14,000-20,000.

Example III

Rosen Modified Sampath-Reddi Assay

A modified version of the rat bone formation assay described in Sampath and Reddi, *Prod. Natl. Acad. Sci. U.S.A.,* 80:6591-6595 (1983) is used to evaluate bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21-49 day old male Long Evans rats. The implants are removed after 7-14 days. Half of each implant is used for alkaline phosphatase analysis [see, A. H. Reddi et al., *Proc. Natl Acad Sci.,* 69:1601 (1972)].

The other half of each implant is fixed and processed for histological analysis. Glycolmethacrylate sections (1 μm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone and matrix. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone.

It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by auto-radiography. The activity is correlated with the protein bands and pI. To estimate the purity of the protein in a particular fraction an extinction coefficient of 1 OD/mg-cm is used as an estimate for protein and the protein is run on SDS PAGE followed by silver staining or radio-iodination and autoradiography.

Example IV

Bovine Protein Composition

The gel slice of the approximate 14,000-20,000 dalton region described in Example IIB is excised and the protein electrophoretically eluted from the gel (Hunkapillar, et al., Supra.). This isolated protein sample is then depleted of SDS [Simpson, et al., *Eur. J. Biochem.* 165:21-29 (1987)] by being bound to a 30×2.1 mm Brownlee RP-18 after dilution with 5 volumes of 90% n-propanol. Protein is recovered by eluting with a step of 40% n-proponal, 0.1% TFA. The fractions containing the eluted protein peak are pooled and brought to near dryness in a savant Speed Vac concentrator. The protein is then re-solubilized with 0.1 M ammonium bicarbonate and digested with 1 μg of TPCK—treated trypsin (Worthington) for 16 hours at 37° C. A second 1 μg dose of trypsin was added and digestion continued for another 4 hours. The resultant digest is then subjected to RPHPLC using a C4 Vydac RPHPLC column and 0.1% TFA-water, 0.1% TFA water-acetonitrile gradient. The resultant peptide peaks were monitored by UV absorbance at 214 and 280 nm and subjected to direct amino terminal amino acid sequence analysis using an Applied Biosystems gas phase sequenator (Model 470A). Three tryptic fragments are isolated by standard procedures having the following amino acid sequence as represented by the amino acid standard three-letter symbols and where the amino acid in parentheses indicates uncertainty in the sequence:

(1). Arg-His-Glu-Leu-Tyr-Val-Ser-Phe-Gln-Asp-Leu-Gly-Trp-Leu-Asp-Trp-Val-Ile-Ala-Pro-Gln-Gly-Tyr (SEQ ID NO: 1)

(2). Leu-Ser-Ala-Thr-Ser-Val-Leu-Tyr-Tyr-Asp-Ser-Ser-Asn-Asn-Val-Ile-Leu-Arg (SEQ ID NO: 2)

(3). Ala-Cys-Cys-Ala-Pro-Thr-Lys (SEQ ID NO: 3)

(4). Thr-Asn-Glu-Leu-Pro-Pro-Pro-Asn-Lys-Leu-Pro-Gly-Ile-Phe-Asp-Asp-Val-His-Gly-Ser-His-Gly-Arg (SEQ ID NO: 4)

The four amino acid sequences identified above share homology with other BMP proteins BMP-2, BMP-3, and BMP-4 disclosed in PCT published applications WO 88/00205 and WO 89/10409, BMP-5, BMP-6, and BMP-7 disclosed in U.S. Ser. Nos. 437,409, 490,033, and 438,919 filed Nov. 15, 1989, Nov. 15, 1989 and Nov. 17, 1989, respectively. Specifically, the above amino acid sequence (1). Arg-His-Glu-Leu-Tyr-Val-Ser-Phe-Gln-Asp-Leu-Gly-Trp-Leu-Asp-Trp-Val-Ile-Ala-Pro-Gln-Gly-Tyr shares homology with BMP-2, BMP-3, BMP-4, BMP-5, BMP-6 and BMP-7 which contain the following human homologous sequence:

BMP-2: Arg-His-Pro-Leu-Tyr-Val-Asp-Phe-Ser-Asp-Val-Gly-Trp-Asn-Asp-Trp-Ile-Val-Ala-Pro-Pro-Gly-Tyr (SEQ ID NO: 16)

BMP-3: Arg-Arg-Tyr-Leu-Lys-Val-Asp-Phe-Ala-Asp-Ile-Gly-Trp-Ser-Glu-Trp-Ile-Ile-Ser-Pro-Lys-Ser-Phe (SEQ ID NO: 17)

BMP-4: Arg-His-Ser-Leu-Tyr-Val-Asp-Phe-Ser-Asp-Val-Gly-Trp-Asn-Asp-Trp-Ile-Val-Ala-Pro-Pro-Gly-Tyr (SEQ ID NO: 18)

BMP-5: Lys-His-Glu-Leu-Tyr-Val-Ser-Phe-Arg-Asp-Leu-Gly-Trp-Gln-Asp-Trp-Ile-Ile-Ala-Pro-Glu-Gly-Tyr (SEQ ID NO: 19)

BMP-6: Lys-His-Glu-Leu-Tyr-Val-Ser-Phe-Gln-Asp-Leu-Gly-Trp-Gln-Asp-Trp-Ile-Ile-Ala-Pro-Lys-Glu-Tyr (SEQ ID NO: 20)

BMP-7: Lys-His-Glu-Leu-Tyr-Val-Ser-Phe-Arg-Asp-Leu-Gly-Trp-Gln-Asp-Trp-Ile-Ile-Ala-Pro-Glu-Gly-Try (SEQ ID NO: 21)

The second amino acid sequence (2). Leu-(Ser)-Ala-Thr-Ser-Val-Leu-Tyr-Tyr-Asp-Ser-Ser-Asn-Asn-Val-Ile-Leu-Arg shares homology with the following human sequences of these BMP molecules:

BMP-2: Leu-Ser-Ala-Ile-Ser-Met-Leu-Tyr-Leu-Asp-Glu-Asn-Glu-Lys-Val-Val-Leu-Lys (SEQ ID NO: 22)

BMP-3: Met-Ser-Ser-Leu-Ser-Ile-Leu-Phe-Phe-Asp-Glu-Asn-Lys-Asn-Val-Val-Leu-Lys (SEQ ID NO: 23)

BMP-4: Leu-Ser-Ala-Ile-Ser-Met-Leu-Tyr-Leu-Asp-Glu-Tyr-Asp-Lys-Val-Val-Leu-Lys (SEQ ID NO: 24)

BMP-5: Leu-Asn-Ala-Ile-Ser-Val-Leu-Tyr-Phe-Asp-Asp-Ser-Ser-Glu-Val-Ile-Leu-Lys (SEQ ID NO: 25)

BMP-6: Leu-Asn-Ala-Ile-Ser-Val-Leu-Tyr-Phe-Asp-Asp-Asn-Ser-Asn-Val-Ile-Leu-Lys (SEQ ID NO: 26)

BMP-7: Leu-Asn-Ala-Ile-Ser-Val-Leu-Tyr-Phe-Asp-Asp-Ser-Ser-Asn-Val-Ile-Leu-Lys (SEQ ID NO: 27)

The third amino acid sequence (3). Ala-Cys-Cys-Ala-Pro-Thr-Lys shares homology with the following human sequences of these BMP molecules:

BMP-2: Ala-Cys-Cys-Val-Pro-Thr-Glu (SEQ ID NO: 28)
BMP-3: Pro-Cys-Cys-Val-Pro-Glu-Lys (SEQ ID NO: 29)
BMP-4: Ala-Cys-Cys-Val-Pro-Thr-Gln (SEQ ID NO: 30)
BMP-5: Pro-Cys-Cys-Ala-Pro-Thr-Lys (SEQ ID NO: 31)
BMP-6: Pro-Cys-Cys-Ala-Pro-Thr-Lys (SEQ ID NO: 32)
BMP-7: Pro-Cys-Cys-Ala-Pro-Thr-Gln (SEQ ID NO: 33)

The fourth amino acid sequence shares some homology (i.e. Asn-Glu-Leu-Pro-) with BMP-3, disclosed in PCT published application WO 88/00205 and WO 89/10409.

It is contemplated that the BMP-8 proteins of the invention will be structurally similar to those BMP proteins BMP-2 through BMP-7. It is contemplated that mature BMP-8 proteins comprise a dimer of disulfide linked polypeptide subunits.

Example V

Isolation of DNA

DNA sequences encoding BMP-8 proteins may be isolated using various techniques known to those skilled in the art. As described below, oligonucleotide probes may be designed on the basis of the amino acid sequence of the above-identified tryptic fragments and synthesized on an automatic DNA synthesizer. The probes may consist of pools of oligonucleotides or unique oligonucleotides designed from the tryptic sequences according to the method of R. Lathe, *J. Mol. Biol.* 183(1):1-12 (1985).

Based on the similarity of the three amino acid sequences described above to BMP-2 through BMP-7 it is contemplated that the BMP-8 proteins of the invention may have a structure in which amino acid sequence (3) and amino acid sequence (2) are located immediately adjacent to each other as follows:

Ala-Cys-Cys-Ala-Pro-Thr-Lys-Leu-(Ser)-Ala-Thr-Ser-Val-Leu-Tyr-Tyr-Asp-Ser-Ser-Asn-Asn-Val-Ile-Leu-Arg

The following four oligonucleotides are designed on the basis of the amino acid sequence of the above identified tryptic fragment [BMP-8 amino acid sequence (2) Leu-(Ser)-Ala-Thr-Ser-Val-Leu-Tyr-Tyr-Asp-Ser-Ser-Asn-Asn-Val-Ile-Leu-Arg] and synthesized on an automated DNA synthesizer.

1: GACTCTAGAATNACRTTRTTNGANG (SEQ ID NO: 34)

2: GACTCTAGAATNACRTTRTTNGARC (SEQ ID NO: 35)

3: GACTCTAGAATNACRTTRTTRCTNG (SEQ ID NO: 36)

4: GACTCTAGAATNACRTTRTTRCTRC (SEQ ID NO: 37)

The first 9 nucleotides of oligonucleotides #1 through #4 (underlined) contain the recognition sequence for the restriction endonuclease XbaI in order to facilitate manipulation of a specifically amplified DNA sequence encoding the BMP-8 protein and thus are not derived from the amino acid sequence (2) presented above.

The following oligonucleotide is designed on the basis of the amino acid sequence of another above identified tryptic fragment [BMP-8 amino acid sequence (3) Ala-Cys-Cys-Ala-Pro-Thr-Lys] and synthesized on an automated DNA synthesizer.

5: GCGGATCCGCNTGYTGYGCNCCNAC (SEQ ID NO: 38)

The first 8 nucleotides of oligonucleotide #5 (underlined) contain the recognition sequence for the restriction endonuclease BamHI and for reasons described above are not derived from the amino acid sequence (3).

The standard nucleotide symbols in the above identified probes are as follows: A,adenosine; C,cytosine; G,guanine; T,thymine; N,adenosine or cytosine or guanine or thymine; R,adenosine or guanine; Y,cytosine or thymine; and H,adenosine or cytosine or thymine.

Oligonucleotides #4 and #5 identified above are utilized as primers to allow the amplification of a specific nucleotide sequence from bovine genomic DNA. The amplification reaction is performed as follows:

Bovine genomic DNA (source: bovine liver) is denatured at 100° C. for 5 minutes and then chilled on ice before adding to a reaction mixture containing 200 µM each deoxynucleotide triphosphates (dATP, dGTP, dCTP and dTTP), 10 mM Tris-HCl pH 8.3, 50 mM KCl, 1.5 mM MgCl$_2$, 0.001% gelatin, 1.25 units Taq DNA polymerase, 100 pM oligonucleotide #4 and 100 pM oligonucleotide #5. This reaction mixture is incubated at 94° C. for 2 minutes and then subjected to thermal cycling in the following manner. 1 minute at 94° C., 1 minute at 40° C., 1 minute at 72° C. for three cycles then 1 minute at 94° C., 1 minute at 55° C., 1 minute at 72° C. for thirty-seven cycles, followed by a 7 minute incubation at 72° C.

The DNA which is specifically amplified by this reaction is ethanol precipitated, digested with the restriction endonucleases XbaI and BamHI and subjected to agarose gel electrophoresis. A region of the gel is excised, the DNA is electroeluted and an 80 base pair product is subcloned into the plasmid vector pGEM3 between the XbaI and BamHI sites of the polylinker. DNA sequence analysis of resulting subclones indicates that the specifically amplified DNA sequences product encodes the amino acid sequences set forth in tryptic fragments (2) and (3).

The DNA sequence (SEQ ID NO: 5) and derived amino acid sequence (SEQ ID NO: 6) of this specifically amplified DNA fragment is as follows:

```
(1)                          (24)
GGATCCGCGTGCTGTGCTCCGAC C AAG CTG AGC GCC ACC TCC GTG CTC TAC
                          Lys Leu Ser Ala Thr Ser Val Leu Tyr

(58)              (80)
TAC GAC AGCAGCAACAATGTAATTCTAGA
Tyr Asp
```

Nucleotides 1-24 of this sequence comprise a portion of oligonucleotide #5 and nucleotides 58-80 comprise a portion of the reverse compliment of oligonucleotide #4 utilized to perform the specific amplification reaction. Due to the function of oligonucleotides #4 and #5 in initiating the amplification reaction, they may not correspond exactly to the actual sequence encoding a BMP-8 protein and are therefore not translated in the above amino acid derivation.

The following oligonucleotide probe is designed on the basis of the bovine DNA sequence set forth above above and synthesized on an automated DNA synthesizer:
  #6:   AAGCTGAGCGCCACCTCCGTGCTCTACTAC
        (SEQ ID NO: 39)

This oligonucleotide probe is radioactively labeled with $^{32}$P and employed to screen a bovine genomic library constructed in the vector λ EMBL3. 400,000 recombinants of the bovine genomic library are plated at a density of 8000 recombinants per plate on 50 plates. Duplicate nitrocellulose replicas of the recombinant bacteriophage plaques are made from these plates and amplified. The oligonucleotide probe #6 is hybridized to the amplified nitrocellulose replicas in SHB (Standard Hybridization Buffer) at 65 degrees C. and washed with 1× SSC, 0.1% SDS at 65 degrees C. Eleven positively hybridizing recombinants are obtained and are plaque purified. Bacteriophage plate stocks are made and bacteriophage DNA is isolated from each of the eleven plaque purified recombinants. The oligonucleotide hybridizing region of one of the recombinants, designated λ 9800-10 is localized to a 0.4 kb PstI fragment. This fragment is subcloned into a plasmid vector (pGEM-3) and DNA sequence analysis performed. The partial DNA sequence (SEQ ID NO: 7) and derived amino acid sequence (SEQ ID NO: 8) of this region of clone λ 9800-10 are shown in Table 1. The bacteriophage λ 9800-10 was deposited with the American Type Culture Collection, 12301 Parklawn Drive, Rockville, Md. "ATCC" under the accession #75011 on May 15, 1991. This deposit meets the requirements of the Budapest Treaty of the International Recognition of the Deposit of Microorganisms for the Purpose of Patent Procedure and Regulations thereunder.

It is noted that nucleotide 95 is a "T" whereas in the amplified DNA fragment described above the corresponding nucleotide is a "C". This λ 9800-10 clone encodes at least a portion of the bovine BMP-8 protein of the invention. The BMP-8 peptide sequence from this clone is 49 amino acids in length and is encoded by the DNA sequence from nucleotide 30 through nucleotide 176. The amino acid sequence corresponding to tryptic fragments (2) and (3) isolated from bovine bone 28 to 30 kD material is underlined in Table 1. An in-frame stop codon (TGA) [nucleotides 177-179] indicates that this clone encodes the carboxy-terminal portion of the bovine BMP-8 protein of the invention. The nucleotides 1-29 are believed to be intron sequences based on the presence of a consensus splice site (a pyrimidine-rich stretch followed by the dinucleotide AG) as well as the lack of homology of the potentially encoded amino acids to other BMP proteins.

The following two oligonucleotides are designed on the basis of the amino sequence of tryptic fragment (1) Arg-His-Glu-Leu-Tyr-Val-Ser-Phe-Gln-Asp-Leu-Gly-Trp-Leu-Asp-Trp-Val-Ile-Ala-Pro-Gln-Gly-Tyr ((SEQ ID NO: 1) described above.
  #7: TGGGTNATHGCNCCNCA (SEQ ID NO: 40)
  #8: ATHGCNCCNCARGGNTA (SEQ ID NO: 41)

These oligonucleotides hybridize to clone λ 9800-10 in SHB at 42 degrees C. with washing in 5× SSC, 0.1% SDS at 42 degrees C. A restriction fragment of clone λ 9800-10 containing the hybridizing region of both oligo #7 and #8 set forth above is subcloned into a plasmid vector (pGEM-3) and DNA sequence analysis performed. The partial DNA sequence (SEQ ID NO: 9) and derived amino acid sequence (SEQ ID NO: 10) of this region of clone λ 9800-10 are shown in Table 2.

TABLE 1

```
                                    30
TGCCCGCTGCCCCCTCCCGCCCCGCCAG GTG CAC CTG CTG AAG CCG CAC GCG
                              Val His Leu Leu Lys Pro His Ala

GTC CCC AAG GCG TGC TGC GCG CCC ACC AAG CTG AGC GCC ACT TCC GTG
Val Pro Lys Ala Cys Cys Ala Pro Thr Lys Leu Ser Ala Thr Ser Val

CTC TAC TAC GAC AGC AGC AAC AAC GTC ATC CTG CGC AAG CAC CGC AAC
Leu Tyr Tyr Asp Ser Ser Asn Asn Val Ile Leu Arg Lys His Arg Asn

176
ATG GTG GTC CGC GCC TGC GGC TGC CAC TGA GGCCCCAACTCCACCGGCAG
MET Val Val Arg Ala Cys Gly Cys His
```

TABLE 2

```
                                                        51
GGGGTGGGAG GGCACGTGGA TGGGACTCAC CTTCTCCCAC TACCCCCAG GAC TGG
                                                     Asp Trp

GTC ATC GCC CCC CAA GGC TAC TCA GCC TAT TAC TGT GAA GGG GAG TGC
Val Ile Ala Pro Gln Gly Tyr Ser Ala Tyr Tyr Cys Glu Gly Glu Cys

TCC TTC CCG CTG GAC TCC TGC ATG AAC GCC ACC AAC CAC GCC ATC CTG
Ser Phe Pro Leu Asp Ser Cys MET Asn Ala Thr Asn His Ala Ile Leu

161
CAG TCC CTG GTCAGTACCTC
Gln Ser Leu
```

This region of clone λ 9800-10 encodes another portion of the bovine BMP-8 protein of the invention. The BMP-8 peptide sequence from this clone is 37 amino acids in length and is encoded by the DNA sequence from nucleotide 51 through nucleotide 161. A portion of the amino acid sequence corresponding to tryptic fragment (1) (SEQ ID NO: 1) isolated from bovine bone 28 to 30 kD material is underlined in Table 2. The nucleotides 1-50 are believed to be intron sequences based on the presence of a consensus splice site and lack of homology of the derived amino acid sequence to the remainder of the tryptic fragment (1). Similarly, the nucleotide sequences 162-172 are also believed to be intron sequences.

Another PstI restriction fragment of clone λ 9800-10 is subcloned and sequenced in a similar manner to that described above. The partial DNA sequence (SEQ ID NO: 11) and derived amino acid sequence (SEQ ID NO: 12) of this region of clone λ 9800-10 are shown in Table 3.

The amino acid sequence corresponding to this tryptic peptide is also underlined in Table 3. The nucleotide sequences 1-19 and 100-120 are believed to be intron sequences on the basis of reasons described previously.

Based on the derived amino acid sequences set forth in Tables 1, 2, and 3, the bovine BMP-8 protein of the invention is contemplated to be comprised of the amino acid sequence present in Table 4 (SEQ ID NO: 15) which corresponds to the sequence of SEQ ID NO: 14 from amino acid position number 31 through position 142 wherein Met at position 97 is replaced with Leu, Asn at position 100 is replaced with His, and Lys at position 137 is replaced with Arg.

TABLE 3

```
               20
CCCTTGCGTGTCCCCGCAG AC GAC GTC CAC GGC TCC CAC GGC CGG CAG GTG

Asp Val His Gly Ser His Gly Arg Gln Val

99
TGC CGT CGG CAC GAG CTG TAC GTG AGC TTC CAG GAC CTG GGC TGG CTG

Cys Arg Arg His Glu Leu Tyr Val Ser Phe Gln Asp Leu Gly Trp Leu

GTGAGTTCCGACTCTCCTTT
```

This region of clone λ 9800-10 encodes another portion of the BMP-8 protein of the invention. The BMP-8 peptide sequence from this clone is 26 amino acids in length and is encoded by the DNA sequence from nucleotide 20 through nucleotide 99. The remaining portion of the amino acid sequence corresponding to tryptic fragments (1) isolated from bovine bone 28 to 30 kD material is underlined in Table 3. It is also noted that this sequence encodes a peptide sequence comprising portion of the tryptic fragment (4) isolated from bovine bone 28 to 30 kD material [(Thr)-Asn-Glu-Leu-Pro-Pro-(Pro)-Asn-Lys-Leu-(Pro)-Gly-Ile-Phe-Asp-Asp-Val-His-Gly-Ser-His-Gly-Arg] (SEQ ID NO: 4).

TABLE 4

```
  1                                      11
Asp Val His Gly Ser His Gly Arg Gln Val Cys Arg Arg His Glu Leu

Tyr Val Ser Phe Gln Asp Leu Gly Trp Leu Asp Trp Val Ile Ala Pro

Gln Gly Tyr Ser Ala Tyr Tyr Cys Glu Gly Glu Cys Ser Phe Pro Leu

Asp Ser Cys Met Asn Ala Thr Asn His Ala Ile Leu Gln Ser Leu Val

His Leu Leu Lys Pro His Ala Val Pro Lys Ala Cys Cys Ala Pro Thr

Lys Leu Ser Ala Thr Ser Val Leu Tyr Tyr Asp Ser Ser Asn Asn Val

Ile Leu Arg Lys His Arg Asn Met Val Val Arg Ala Cys Gly Cys His
                                                              112
```

This sequence is realized to be homologous to other BMP proteins. For example, the carboxy-terminal cysteine-rich region (amino acids #11 through #112 of Table 4 (SEQ ID NO: 15)) demonstrate the following amino acid identities: 55% to BMP-2; 41% to BMP-3; 55% to BMP-4; 74% to BMP-5; 75% to BMP-6; and 75% to BMP-7.

Example V

Human BMP-8

A 0.4 kb PstI bovine genomic BMP-8 fragment comprising the sequence set forth in Table 1 is radioactively labeled with $^{32}$P and used as a probe to screen a human genomic library [Strategene Cloning Systems (catalog #944201)] constructed in the vector λ FIX. 1,000,000 recombinants of this human genomic library are plated at a density of 20,000 bacteriophage per plate. Duplicate nitrocellulose replicas of the recombinant bacteriophage plaques are made and hybridized to the bovine genomic probe in SHB at 65 degrees C. and washed with 0.2× SSC, 0.1% SDS at 65 degrees C. Twenty-five positives are obtained and replated for secondaries.

The following oligonucleotide probe is designed on the basis of nucleotide #57 through nucleotide #86 of the DNA sequence set forth in Table 2 and synthesized on an automated DNA synthesizer.

9: GTCATCGCCCCCAAGGCTACTCAGCCTAT (SEQ ID NO: 42)

The following oligonucleotide probe is designed on the basis of nucleotide #20 through nucleotide #43 of the DNA sequence set forth in Table 3 and synthesized on an automated DNA synthesizer.

10: ACGACGTCCACGGCTCCCACGGCC (SEQ ID NO: 43)

One set of secondary filters is hybridized to probe #9 in SHB at 65 degrees C. and washed in 1× SSC, 0.1% SDS at 65 degrees C., the other set of secondary filters are hybridized to probe #10 in SHB at 50 degrees C. and washed in 5× SSC; 0.1% SDS at 50 degrees C. Two clones are found to hybridize to both oligonucleotide probes. The positive hybridization of oligonucleotides #9 and #10 to these two human genomic clones indicates that they contain at least a portion of the nucleotide sequence encoding the human equivalent of the BMP-8 protein of the invention. One of these clones is designated λ H8 12-1 and the bacteriophage was deposited with American Type Culture Collection, 12301 Parklawn Drive, Rockville, Md., U.S.A. "ATCC" under the accession #75010 on May 15, 1991. This deposit meets the requirements of the Budapest Treaty of the International Recognition of the Deposit of Microorganisms for the Purpose of Patent Procedure and Regulations thereunder.

Once a recombinant bacteriophage containing DNA encoding a portion of the human cartilage and/or bone inductive factor molecule is obtained, the human coding sequence can be used as a probe to identify a human cell line or tissue which synthesizes the bone inductive factor. Alternatively, the bovine coding sequence can be used as a probe to identify such human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence of the bovine or human cartilage and/or bone inductive protein. mRNA is selected by oligo (dT) cellulose chromatography and cDNA is synthesized and cloned in lambda gt10 by established techniques (Toole et al., supra).

The following oligonucleotide probe is designed on the basis of the DNA sequence of human genomic clone λ H8 12-1 and synthesized on an automated DNA synthesizer:

11: AGACCTGCCGGCCGTGGGAGCCGTGGACGA (SEQ ID NO: 44)

Approximately 1,000,000 recombinants of a human heart cDNA library (Stratagene catalog #936208) are plated at a density of 20,000 recombinants per plate on 50 plates. Duplicate nitrocellulose replicas of the recombinant bacteriophage plaques are made from these plates and hybridized to oligonucleotide probe #11. Hybridization is performed in SHB at 65 degrees C., and washing is done at 65 degrees C. with 0.1× SSC, 0.1% SDS. A positively hybridizing recombinant is obtained and plaque purified. The insert of this clone is automatically excised and recircularized to generate subclones in the plasmid pBluescript SK- according to the protocol detailed by the manufacturer (Stratagene). This plasmid subclone is designated hH38. Clone hH38 was deposited with the American Type Culture Collection (ATCC), 12301 Parklawn Drive, Rockville, Md., U.S.A., under the accession number 69778 on Mar. 30, 1995. DNA sequence analysis of the insert is set forth in SEQ ID NOS: 13 and 14. This DNA sequence contains an open reading frame of 843 base pairs which encodes a 281 amino acid partial BMP-8 protein. It is expected that the 281 amino acids set forth in SEQ ID NO: 14 represents a portion of the primary translation product which is processed to an active mature protein sequence. The processing of BMP-8 into the mature form is expected to involve dimerization and removal of the N-terminal region in a manner analogous to the processing of the related protein TGF-β [L. E. Gentry, et al., *Molec. & Cell. Biol.* 8:4162 (1988); R. Derynck, et al., *Nature* 316:701 (1985)]. It is comtemplated that an active mature BMP-8 comprises a disulfide linked dimer comprising subunits of amino acid sequences comprising amino acid #4-#142 of SEQ ID NO: 14. Further species may comprise other amino termini of selected from the sequence of SEQ ID NO: 14.

The DNA sequence of this clone as shown in SEQ ID NO: 13 can be utilized by one skilled in the art to design probes for further screening as described above to obtain clones encoding the complete BMP-8 protein.

Additional methods known to those skilled in the art may be used to isolate the human and other species' cartilage/bone proteins of the invention. The procedures described above may be employed to isolate other related proteins of interest by utilizing the bovine or human proteins as a probe source. Such other proteins may find similar utility in, inter alia, fracture repair, wound healing and tissue repair.

Example VI

Expression of the Cartilage/Bone Proteins

In order to produce bovine, human or other mammalian proteins of the invention, the DNA encoding it, isolated as described above, is transferred into an appropriate expression vector and introduced into mammalian cells or other preferred eukaryotic or prokaryotic hosts by conventional genetic engineering techniques. Methods of transfection include electroporation, $CaPO_4$ precipitation, protoplast fusion, microinjection and lipofection. Once the host cells are transformed, stable transformants are then screened for expression of the product by standard immunological, biological or enzymatic assays. The presence of this DNA and mRNA encoding the BMP-8 polypeptides may be detected by standard procedures such as Southern and Northern blotting, high expressing cell lines are cloned or recloned at the appropriate level of selectivity to obtain a more homologous population of cells.

Selected transformed host cells are cultured and the BMP-8 proteins of the invention expressed thereby are recovered, isolated and purified. Characterization of the expressed proteins is carried out using standard techniques. For example characterization may include pulse labeling with [35 S] methionine or cysteine and analysis by polyacrylamide electrophoresis. The recombinantly expressed BMP-8 proteins are free of proteinaceous materials with which they are coproduced and with which they ordinarily are associated in nature, as well as from other contaminants, such as materials found in the cellular media.

It is contemplated that the preferred expression system for biologically active recombinant human proteins of the invention will be stably transformed mammalian cells. For transient expression the cell line of choices is expected to be SV40 transformed African green monkey kidney COS-1 in COS-7 which typically produce moderate amounts of the protein encoded within the plasmid for a period of 1-4 days. It is further contemplated that the preferred mammalian cells will be CHO cells.

One skilled in the art can construct mammalian expression vectors by employing the DNA sequences of the invention sequences and known vectors, such as pCD [Okayama et al., *Mol. Cell Biol.*, 2:161-170 (1982)] and pJL3, pJL4 [Gough et al., *EMBO J.*, 4:645-653 (1985)]. Human BMP-8 may be produced using, the DNA sequence from nucleotide #8 to #853 of SEQ ID NO: 13. The transformation of these vectors into appropriate host cells may result in expression of the proteins of the invention.

One skilled in the art could manipulate the sequence of the invention by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-from or altering nucleotides therein by other known techniques). The modified coding sequence could then be inserted into a known bacterial vector using procedures such as described in T. Taniguchi et al., *Proc. Natl Acad. Sci. USA*, 77:5230-5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO 86/00639 and European patent application EPA 123,289].

A method for producing high levels of a protein of the invention from mammalian cells involves the construction of cells containing multiple copies of the heterologous gene encoding proteins of the invention. The heterologous gene may be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601-629 (1982). This approach can be employed with a number of different cell types. For example, a plasmid containing a DNA sequence for a protein of the invention in operative association with other plasmid sequences enabling expression thereof and the DHFR expression plasmid pAdA26SV(A)3 [Kaufman and Sharp, *Mol. Cell. Biol.*, 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., *Mol Cell Biol.*, 5:1750 (1983). Transformants are cloned, and the proteins of the invention are recovered, isolated, and purified from the culture medium. Biologically active protein expression is monitored by the Rosen-modified Sampath—Reddi rat bone formation assay described above in Example III. Protein expression should increase with increasing levels of MTX resistance. Similar procedures can be followed to produce other related proteins.

Example VII

Biological Activity of Expressed Cartilage/Bone Proteins

To measure the biological activity of the expressed BMP-8 proteins obtained in Example VI above, the protein may be partially purified on a Heparin Sepharose column and further purified using standard purification techniques known to those skilled in the art. For example, post transfection conditioned medium supernatant collected from the cultures may be concentrated by ultrafiltration, dialyzed and applied to a Heparin Sepharose column.

Further purification may be achieved by preparative NaDodSO$_4$/PAGE [Laemmli, *Nature* 227:680-685 (1970)]. For instance, the protein is applied to a gel. Recovery may be estimated by adding L-[$^{35}$S]methionine-labeled BMP protein purified over heparin-Sepharose as described above. Protein may be visualized by copper staining of an adjacent lane [Lee, et al., *Anal. Biochem.* 166:308-312 (1987)]. Appropriate bands are excised and extracted.

The appropriate amount of the resulting solution is mixed with 20 mg of rat matrix and then assayed for in vivo bone and/or cartilage formation activity by the Rosen-modified Sampath—Reddi assay. A mock transfection supernatant fractionation is used as a control. The implants containing rat matrix to which specific amounts of human proteins of the invention have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A purified BMP-8 protein characterized by:
(a) at least one of the following sequences:
　i) Arg-His-Glu-Leu-Tyr-Val-Ser-Phe-Gln-Asp-Leu-Gly-Trp-Leu-Asp-Trp-Val-Ile-Ala-Pro-Gln-Gly-Tyr (SEQ ID NO: 1);
　ii) Leu-Ser-Ala-Thr-Ser-Val-Leu-Tyr-Tyr-Asp-Ser-Ser-Asn-Asn-Val-Ile-Leu-Arg (SEQ ID NO: 2); and
　iii) Ala-Cys-Cys-Ala-Pro-Thr-Lys (SEQ ID NO: 3);
(b) a molecular weight of 28,000-38,000 daltons as determined by sodium dodecyl sulfate polyacrylamide gel electrophoresis; and
(c) a molecular weight of 14,400-20,000 daltons under reducing conditions as determined by sodium dodecyl sulfate polyacrylamide gel electrophoresis said protein being a disulfide linked dimer wherein each of the subunits contains the sequences set forth in part (a) and said protein having the ability to induce the formation of cartilage and/or bone.

2. A pharmaceutical formulation for bone and/or cartilage formation comprising an effective amount of a BMP-8 protein of claim 1 in a pharmaceutically acceptable vehicle.

3. A composition of claim 2 further comprising a matrix for supporting said composition and providing a surface for bone and/or cartilage formation.

4. The composition of claim 3 wherein said matrix comprises a material selected from the group consisting of hydroxyapatite, collagen, polylactic acid and tricalcium phosphate.

5. A pharmaceutical composition for wound healing and tissue repair said composition comprising an effective amount of a BMP-8 protein of claim 1 in a pharmaceutically acceptable vehicle.

6. The BMP-8 protein of claim 1, wherein the BMP-8 is human BMP-8.

* * * * *

SEQUENCE LISTING

```
(1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (F) TISSUE TYPE: Bone (xi) SEQUENCE DESCRIPTION: SEQ ID NO:1:

Arg His Glu Leu Tyr Val Ser Phe Gln Asp Leu Gly Trp Leu Asp Trp
1               5                  10                  15

Val Ile Ala Pro Gln Gly Tyr
            20

(2) INFORMATION FOR SEQ ID NO:2:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Bos taurus
        (F) TISSUE TYPE: Bone (xi) SEQUENCE DESCRIPTION: SEQ ID NO:2:

Leu Ser Ala Thr Ser Val Leu Tyr Tyr Asp Ser Ser Asn Asn Val Ile
```

```
                 1               5              10              15
Leu Arg (2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bos taurus
        (F) TISSUE TYPE: Bone (xi) SEQUENCE DESCRIPTION: SEQ ID NO:3:

Ala Cys Cys Ala Pro Thr Lys
1               5

(2) INFORMATION FOR SEQ ID NO:4:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (iii) HYPOTHETICAL: NO (vi) ORIGINAL SOURCE:
        (A) ORGANISM: Bos taurus
        (F) TISSUE TYPE: Bone (xi) SEQUENCE DESCRIPTION: SEQ ID NO:4:

Thr Asn Glu Leu Pro Pro Pro Asn Lys Leu Pro Gly Ile Phe Asp Asp
1               5                   10                  15

Val His Gly Ser His Gly Arg
                20

(2) INFORMATION FOR SEQ ID NO:5:

(i) SEQUENCE CHARACTERISTICS:
        (A) LENGTH: 80 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bos taurus (vii) IMMEDIATE SOURCE:
        (B) CLONE: acc30

(viii) POSITION IN GENOME:
        (C) UNITS: bp (ix) FEATURE:
        (A) NAME/KEY: CDS
```

(B) LOCATION: 25..57

(xi) SEQUENCE DESCRIPTION: SEQ ID NO:5:

```
GGATCCGCGT GCTGTGCTCC GACC AAG CTG AGC GCC ACC TCC GTG CTC TAC        51
                           Lys Leu Ser Ala Thr Ser Val Leu Tyr
                            1               5

TAC GAC AGCAGCAACA ATGTAATTCT AGA                                     80
Tyr Asp
 10
```

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:6:

```
Lys Leu Ser Ala Thr Ser Val Leu Tyr Tyr Asp
 1               5                  10
```

(2) INFORMATION FOR SEQ ID NO:7:

(i) SEQUENCE CHARACTERISTICS:
        (A) LENGTH: 199 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Bos taurus (vii) IMMEDIATE SOURCE:
        (A) LIBRARY: Bovine genomic
        (B) CLONE: Lambda 9800-10

(viii) POSITION IN GENOME:
        (C) UNITS: bp (ix) FEATURE:
        (A) NAME/KEY: exon
        (B) LOCATION: 30..199

(ix) FEATURE:
        (A) NAME/KEY: intron
        (B) LOCATION: 1..29

(ix) FEATURE:
        (A) NAME/KEY: CDS
        (B) LOCATION: 30..179

(xi) SEQUENCE DESCRIPTION: SEQ ID NO:7:

```
TGCCCGCTGC CCCCTCCCGC CCCCGCCAG GTG CAC CTG CTG AAG CCG CAC GCG        53
                                Val His Leu Leu Lys Pro His Ala
                                 1               5

GTC CCC AAG GCG TGC TGC GCG CCC ACC AAG CTG AGC GCC ACT TCC GTG       101
Val Pro Lys Ala Cys Cys Ala Pro Thr Lys Leu Ser Ala Thr Ser Val
 10              15                  20

CTC TAC TAC GAC AGC AGC AAC AAC GTC ATC CTG CGC AAG CAC CGC AAC       149
Leu Tyr Tyr Asp Ser Ser Asn Asn Val Ile Leu Arg Lys His Arg Asn
 25                  30                  35                  40

ATG GTG GTC CGC GCC TGC GGC TGC CAC TGAGGCCCCA ACTCCACCGG             196
Met Val Val Arg Ala Cys Gly Cys His
             45                  50
```

```
CAG                                                                       199

(2) INFORMATION FOR SEQ ID NO:8:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO:8:

Val His Leu Leu Lys Pro His Ala Val Pro Lys Ala Cys Cys Ala Pro
 1               5                  10                  15

Thr Lys Leu Ser Ala Thr Ser Val Leu Tyr Tyr Asp Ser Ser Asn Asn
                20                  25                  30

Val Ile Leu Arg Lys His Arg Asn Met Val Val Arg Ala Cys Gly Cys
        35                  40                  45

His (2) INFORMATION FOR SEQ ID NO:9:

(i) SEQUENCE CHARACTERISTICS:
        (A) LENGTH: 172 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Bos taurus (vii) IMMEDIATE SOURCE:
        (A) LIBRARY: Bovine genomic
        (B) CLONE: Lambda 9800-10

(viii) POSITION IN GENOME:
        (C) UNITS: bp (ix) FEATURE:
        (A) NAME/KEY: exon
        (B) LOCATION: 51..161

(ix) FEATURE:
        (A) NAME/KEY: intron
        (B) LOCATION: 1..50

(ix) FEATURE:
        (A) NAME/KEY: intron
        (B) LOCATION: 162..172

(ix) FEATURE:
        (A) NAME/KEY: CDS
        (B) LOCATION: 51..161

(xi) SEQUENCE DESCRIPTION: SEQ ID NO:9:

GGGGTGGGAG GGCACGTGGA TGGGACTCAC CTTCTCCCAC TACCCCCCAG GAC TGG        56
                                                        Asp Trp
                                                         1

GTC ATC GCC CCC CAA GGC TAC TCA GCC TAT TAC TGT GAA GGG GAG TGC       104
Val Ile Ala Pro Gln Gly Tyr Ser Ala Tyr Tyr Cys Glu Gly Glu Cys
     5                  10                  15

TCC TTC CCG CTG GAC TCC TGC ATG AAC GCC ACC AAC CAC GCC ATC CTG       152
Ser Phe Pro Leu Asp Ser Cys Met Asn Ala Thr Asn His Ala Ile Leu
        20                  25                  30
```

```
CAG TCC CTG GTCAGTACCT C                                                172
Gln Ser Leu
 35
```

(2) INFORMATION FOR SEQ ID NO:10:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:10:

```
Asp Trp Val Ile Ala Pro Gln Gly Tyr Ser Ala Tyr Tyr Cys Glu Gly
 1               5                  10                  15

Glu Cys Ser Phe Pro Leu Asp Ser Cys Met Asn Ala Thr Asn His Ala
             20                  25                  30

Ile Leu Gln Ser Leu
         35
```

(2) INFORMATION FOR SEQ ID NO:11:

(i) SEQUENCE CHARACTERISTICS:
        (A) LENGTH: 119 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Bos taurus (vii) IMMEDIATE SOURCE:
        (A) LIBRARY: Bovine genous
        (B) CLONE: Lambda 9800-10

(viii) POSITION IN GENOME:
        (C) UNITS: bp (ix) FEATURE:
        (A) NAME/KEY: exon
        (B) LOCATION: 20..99

(ix) FEATURE:
        (A) NAME/KEY: intron
        (B) LOCATION: 1..19

(ix) FEATURE:
        (A) NAME/KEY: intron
        (B) LOCATION: 100..119

(ix) FEATURE:
        (A) NAME/KEY: CDS
        (B) LOCATION: 22..99

(xi) SEQUENCE DESCRIPTION: SEQ ID NO:11:

```
CCCTTGCGTG TCCCCGCAGA C GAC GTC CAC GGC TCC CAC GGC CGG CAG GTG      51
                       Asp Val His Gly Ser His Gly Arg Gln Val
                        1               5                  10

TGC CGT CGG CAC GAG CTG TAC GTG AGC TTC CAG GAC CTG GGC TGG CTG      99
Cys Arg Arg His Glu Leu Tyr Val Ser Phe Gln Asp Leu Gly Trp Leu
             15                  20                  25

GTGAGTTCCG ACTCTCCTTT                                                119
```

(2) INFORMATION FOR SEQ ID NO:12:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:12:

Asp Val His Gly Ser His Gly Arg Gln Val Cys Arg Arg His Glu Leu
 1               5                  10                  15

Tyr Val Ser Phe Gln Asp Leu Gly Trp Leu
            20                  25

(2) INFORMATION FOR SEQ ID NO:13:

(i) SEQUENCE CHARACTERISTICS:
        (A) LENGTH: 1003 base pairs
        (B) TYPE: nucleic acid
        (C) STRANDEDNESS: double
        (D) TOPOLOGY: circular (ii) MOLECULE TYPE: cDNA to mRNA (iii) HYPOTHETICAL: NO (vi) ORIGINAL SOURCE:
        (A) ORGANISM: Hopmo sapiens
        (F) TISSUE TYPE: Human Heart (vii) IMMEDIATE SOURCE:
        (A) LIBRARY: Human heart cDNA library stratagene catalog
            #936208
        (B) CLONE: hH38

(viii) POSITION IN GENOME:
        (C) UNITS: bp (ix) FEATURE:
        (A) NAME/KEY: CDS
        (B) LOCATION: 8..850

(ix) FEATURE:
        (A) NAME/KEY: mat_peptide
        (B) LOCATION: 427..843

(ix) FEATURE:
        (A) NAME/KEY: mRNA
        (B) LOCATION: 1..997

(xi) SEQUENCE DESCRIPTION: SEQ ID NO:13:

GAATTCC GAG CCC CAT TGG AAG GAG TTC CGC TTT GAC CTG ACC CAG ATC         49
        Glu Pro His Trp Lys Glu Phe Arg Phe Asp Leu Thr Gln Ile
        -139            -135                -130

CCG GCT GGG GAG GCG GTC ACA GCT GCG GAG TTC CGG ATT TAC AAG GTG         97
Pro Ala Gly Glu Ala Val Thr Ala Ala Glu Phe Arg Ile Tyr Lys Val
-125                -120                -115                -110

CCC AGC ATC CAC CTG CTC AAC AGG ACC CTC CAC GTC AGC ATG TTC CAG        145
Pro Ser Ile His Leu Leu Asn Arg Thr Leu His Val Ser Met Phe Gln
                -105                -100                -95

GTG GTC CAG GAG CAG TCC AAC AGG GAG TCT GAC TTG TTC TTT TTG GAT        193
Val Val Gln Glu Gln Ser Asn Arg Glu Ser Asp Leu Phe Phe Leu Asp
            -90                 -85                 -80

CTT CAG ACG CTC CGA GCT GGA GAC GAG GGC TGG CTG GTG CTG GAT GTC        241
Leu Gln Thr Leu Arg Ala Gly Asp Glu Gly Trp Leu Val Leu Asp Val
        -75                 -70                 -65

ACA GCA GCC AGT GAC TGC TGG TTG CTG AAG CGT CAC AAG GAC CTG GGA        289
Thr Ala Ala Ser Asp Cys Trp Leu Leu Lys Arg His Lys Asp Leu Gly
    -60                 -55                 -50

CTC CGC CTC TAT GTG GAG ACT GAG GAT GGG CAC AGC GTG GAT CCT GGC        337

-continued

```
Leu Arg Leu Tyr Val Glu Thr Glu Asp Gly His Ser Val Asp Pro Gly
-45                 -40                 -35                 -30

CTG GCC GGC CTG CTG GGT CAA CGG GCC CCA CGC TCC CAA CAG CCT TTC      385
Leu Ala Gly Leu Leu Gly Gln Arg Ala Pro Arg Ser Gln Gln Pro Phe
                -25                 -20                 -15

GTG GTC ACT TTC TTC AGG GCC AGT CCG AGT CCC ATC CGC ACC CCT CGG      433
Val Val Thr Phe Phe Arg Ala Ser Pro Ser Pro Ile Arg Thr Pro Arg
            -10                  -5                   1

GCA GTG AGG CCA CTG AGG AGG AGG CAG CCG AAG AAA AGC AAC GAG CTG      481
Ala Val Arg Pro Leu Arg Arg Arg Gln Pro Lys Lys Ser Asn Glu Leu
         5                  10                  15

CCG CAG GCC AAC CGA CTC CCA GGG ATC TTT GAT GAC GTC CAC GGC TCC      529
Pro Gln Ala Asn Arg Leu Pro Gly Ile Phe Asp Asp Val His Gly Ser
 20                  25                  30                  35

CAC GGC CGG CAG GTC TGC CGT CGG CAC GAG CTC TAC GTC AGC TTC CAG      577
His Gly Arg Gln Val Cys Arg Arg His Glu Leu Tyr Val Ser Phe Gln
             40                  45                  50

GAC CTT GGC TGG CTG GAC TGG GTC ATC GCC CCC CAA GGC TAC TCA GCC      625
Asp Leu Gly Trp Leu Asp Trp Val Ile Ala Pro Gln Gly Tyr Ser Ala
                 55                  60                  65

TAT TAC TGT GAG GGG GAG TGC TCC TTC CCG CTG GAC TCC TGC ATG AAC      673
Tyr Tyr Cys Glu Gly Glu Cys Ser Phe Pro Leu Asp Ser Cys Met Asn
             70                  75                  80

GCC ACC AAC CAC GCC ATC CTG CAG TCC CTG GTG CAC CTG ATG AAG CCA      721
Ala Thr Asn His Ala Ile Leu Gln Ser Leu Val His Leu Met Lys Pro
 85                  90                  95

AAC GCA GTC CCC AAG GCG TGC TGT GCA CCC ACC AAG CTG AGC GCC ACC      769
Asn Ala Val Pro Lys Ala Cys Cys Ala Pro Thr Lys Leu Ser Ala Thr
100                 105                 110                 115

TCT GTG CTC TAC TAT GAC AGC AGC AAC AAC GTC ATC CTG CGC AAG CAC      817
Ser Val Leu Tyr Tyr Asp Ser Ser Asn Asn Val Ile Leu Arg Lys His
                120                 125                 130

CGC AAC ATG GTG GTC AAG GCC TGC GGC TGC CAC TGAGTCAGCC CGCCCAGCCC    870
Arg Asn Met Val Val Lys Ala Cys Gly Cys His
            135                 140

TACTGCAGCC ACCCTTCTCA TCTGGATCGG GCCCTGCAGA GGCAGAAAAC CCTTAAATGC    930

TGTCACAGCT CAAGCAGGAG TGTCAGGGGC CCTCACTCTC GGTGCCTACT TCCTGTCAGG    990

CTTCTGGGAA TTC                                                      1003
```

(2) INFORMATION FOR SEQ ID NO:14:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:14:

```
Glu Pro His Trp Lys Glu Phe Arg Phe Asp Leu Thr Gln Ile Pro Ala
-139                -135                -130                -125

Gly Glu Ala Val Thr Ala Ala Glu Phe Arg Ile Tyr Lys Val Pro Ser
            -120                -115                -110

Ile His Leu Leu Asn Arg Thr Leu His Val Ser Met Phe Gln Val Val
        -105                -100                 -95

Gln Glu Gln Ser Asn Arg Glu Ser Asp Leu Phe Phe Leu Asp Leu Gln
         -90                 -85                 -80

Thr Leu Arg Ala Gly Asp Glu Gly Trp Leu Val Leu Asp Val Thr Ala
 -75                 -70                 -65                 -60
```

```
Ala Ser Asp Cys Trp Leu Leu Lys Arg His Lys Asp Leu Gly Leu Arg
            -55                 -50                 -45

Leu Tyr Val Glu Thr Glu Asp Gly His Ser Val Asp Pro Gly Leu Ala
            -40                 -35                 -30

Gly Leu Leu Gly Gln Arg Ala Pro Arg Ser Gln Gln Pro Phe Val Val
            -25                 -20                 -15

Thr Phe Phe Arg Ala Ser Pro Ser Pro Ile Arg Thr Pro Arg Ala Val
            -10                  -5                   1                   5

Arg Pro Leu Arg Arg Gln Pro Lys Lys Ser Asn Glu Leu Pro Gln
                 10                  15                  20

Ala Asn Arg Leu Pro Gly Ile Phe Asp Asp Val His Gly Ser His Gly
             25                  30                  35

Arg Gln Val Cys Arg Arg His Glu Leu Tyr Val Ser Phe Gln Asp Leu
             40                  45                  50

Gly Trp Leu Asp Trp Val Ile Ala Pro Gln Gly Tyr Ser Ala Tyr Tyr
         55                  60                  65

Cys Glu Gly Glu Cys Ser Phe Pro Leu Asp Ser Cys Met Asn Ala Thr
 70                  75                  80                  85

Asn His Ala Ile Leu Gln Ser Leu Val His Leu Met Lys Pro Asn Ala
             90                  95                 100

Val Pro Lys Ala Cys Cys Ala Pro Thr Lys Leu Ser Ala Thr Ser Val
            105                 110                 115

Leu Tyr Tyr Asp Ser Ser Asn Asn Val Ile Leu Arg Lys His Arg Asn
            120                 125                 130

Met Val Val Lys Ala Cys Gly Cys His
        135                 140

(2) INFORMATION FOR SEQ ID NO:15:

(i) SEQUENCE CHARACTERISTICS:
        (A) LENGTH: 112 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:15:

Asp Val His Gly Ser His Gly Arg Gln Val Cys Arg Arg His Glu Leu
 1               5                  10                  15

Tyr Val Ser Phe Gln Asp Leu Gly Trp Leu Leu Leu Val Ile Ala Pro
             20                  25                  30

Gln Gly Tyr Ser Ala Tyr Tyr Cys Glu Gly Glu Cys Ser Phe Pro Leu
             35                  40                  45

Asp Ser Cys Met Asn Ala Thr Asn His Ala Ile Leu Gln Ser Leu Val
 50                  55                  60

His Leu Leu Lys Pro His Ala Val Pro Lys Ala Cys Cys Ala Pro Thr
 65                  70                  75                  80

Lys Leu Ser Ala Thr Ser Val Leu Tyr Tyr Asp Ser Ser Asn Asn Val
             85                  90                  95

Ile Leu Arg Lys His Arg Asn Met Val Val Arg Ala Cys Gly Cys His
            100                 105                 110
```